(12) United States Patent
Averback

(10) Patent No.: US 6,309,892 B1
(45) Date of Patent: *Oct. 30, 2001

(54) ANTIBODIES TO COMPONENTS OF DENSE MICROSPHERES AND METHODS OF USING THE SAME

(75) Inventor: Paul Averback, Beaconsfield (CA)

(73) Assignee: Nymox Pharmaceutical Corporation, Quebec (CA)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/660,886

(22) Filed: Jun. 10, 1996

Related U.S. Application Data

(60) Division of application No. 08/168,250, filed on Dec. 17, 1993, now Pat. No. 5,525,339, which is a continuation-in-part of application No. 08/077,641, filed on Jun. 17, 1993, now abandoned, which is a continuation of application No. 07/493,276, filed on Jun. 14, 1990, now Pat. No. 5,231,170, which is a continuation-in-part of application No. 07/315,796, filed on Feb. 27, 1989, now Pat. No. 4,919,915, which is a continuation of application No. 07/021,242, filed on Mar. 3, 1987, now Pat. No. 4,816,416, which is a continuation-in-part of application No. 06/901,007, filed on Aug. 27, 1986, now abandoned.

(51) Int. Cl.$^7$ .................................................. G01N 33/53

(52) U.S. Cl. ........................ 436/518; 436/524; 436/528; 435/7.1; 435/7.92; 435/7.95

(58) Field of Search .............................. 530/387.1, 388.1, 530/389.1, 391.1, 391.3, 300, 350; 435/7.1, 7.9, 7.92, 7.93, 7.94, 7.95; 436/518, 524, 528, 530, 547

(56) References Cited

U.S. PATENT DOCUMENTS

| | | |
|---|---|---|
| 4,816,416 * | 3/1989 | Averback . |
| 4,919,915 * | 4/1990 | Averback . |
| 5,100,645 | 3/1992 | Ali-Khan et al. . |
| 5,231,170 * | 7/1993 | Averback . |
| 5,234,814 * | 8/1993 | Card et al. . |
| 5,262,332 * | 11/1993 | Selkoe et al. . |
| 5,441,870 * | 8/1995 | Seubert et al. . |
| 5,525,339 * | 6/1996 | Averback . |
| 5,567,720 * | 10/1996 | Averback . |
| 5,593,846 * | 1/1997 | Schenk et al. . |
| 5,721,130 * | 2/1998 | Seubert et al. . |

FOREIGN PATENT DOCUMENTS 281922    9/1988    (EP) .

OTHER PUBLICATIONS

Harlow et al "Antibodies: A Laboratory Manual", Cold Spring Harbor Laboratory, 1988 pp. 37 and 55.*

Strittmatter et al, Proc. Natl. Acad. Sci 90:1977–1981, Mar. 1993.*

Chong et al, Life Sci, 47(13):1163–1170, 1990.* van Gool et al, JACS, 39:1025–1039, 1991.*

Averback, Morphometric and Anatomical Correlation of Dense Microsphere and Senile Plaque Formation . . . , The Canadian Journal of Neurological Sciences 9(2) 283–284 (May 1982).

Averback, The Dense Microsphere: "A Newly Delineated Origin of the Senile Plaque in Human Brain" 9(2):284 (May 1982).

Averback, Ultrastructural Studies of the Origin and Growth of Dense Microsphere in Normal Human . . . Canadian Journal of Neurological Sciences 9(2): 290–291 (May 1982).

Averback, Quantitative Correlations of Dense Microspheres and Senile Plaques in Alzheimer Disease, Neurology 32(2): A227 (1982).

Averback, "Immunofluorescent Staining of Dense Microspheres in Human Brain", Arch Pathol Lab Med vol. 106, Aug. 1982 106: 394–396.

Gaskin, "Autoantibodies to Neurofibrillary Tangles and Brain Tissue in Alzeheimer's Disease", Journal Ex. Med. 165:245–250 (Jan. 1987).

Davies, "Preparation of Antigens From Tissues and Fluids", Handbook of Experimental Immunology, 3rd Edition, Blackwell Scientific Publications, (1978), p. 4.1–4.16.

Laemmli, "Cleavage of Structural Proteins During the Assembly of the Head of Bacteriophage T4", Nature, vol. 227:680–685 (1970).

* cited by examiner

Primary Examiner—Patricia A. Duffy
(74) Attorney, Agent, or Firm—Foley & Lardner

(57) ABSTRACT

DMS present in the brain of individuals susceptible to cerebral amyloidosis disintegrate into DMS components to form cerebral amyloid plaques and other DMS components that are removed from the brain via circulating bodily fluids. Detecting the presence of these removed DMS components and/or antibodies thereto in circulating bodily fluids provides a diagnostic mechanism to determine the onset of cerebral amyloid plaque formation. Detecting the presence of these removed DMS components and/or antibodies thereto in circulating bodily fluids also provides a diagnostic mechanism to determine the efficacy of treatment regimes for preventing cerebral amyloid plaque formation. Antibodies also can be raised against isolated DMS components and subsequently utilized in a diagnostic method capable of detecting the onset of cerebral amyloid plaque formation.

7 Claims, 1 Drawing Sheet

ANTIBODIES TO COMPONENTS OF DENSE MICROSPHERES AND METHODS OF USING THE SAME

This is a divisional application based on U.S. Ser. No. 08/168,250 (filed Dec. 17, 1993) now U.S. Pat. No. 5,525,339, which is a continuation-in-part based on U.S. Ser. No. 08/077,641 (filed Jun. 17, 1993) now abandoned, which is a continuation of U.S. Ser. No. 07/493,276 (filed Jun. 14, 1990), now U.S. Pat. No. 5,231,170, which is a continuation-in-part of U.S. Ser. No. 07/315,796 (filed Feb. 27, 1989) now U.S. Pat. No. 4,919,915, which is a continuation of U.S. Ser. No. 07/021,242 (filed Mar. 3, 1987), now U.S. Pat. No. 4,816,416, which in turn is a continuation-in-part of U.S. Ser. No. 06/901,007 (filed Aug. 27, 1986), now abandoned. The respective contents of the aforementioned prior applications are hereby incorporated by reference.

BACKGROUND OF THE INVENTION

The present invention relates to compositions consisting essentially of dense microsphere (DMS) components. The invention also relates to methods for detecting components of DMS in blood, cerebrospinal fluid and other body fluids that result from the disruption of DMS in the brain parenchyma. More specifically, the present invention relates to the correlation of the presence of DMS components in such fluids and the onset or progression of the cerebral amyloid formation associated with Alzheimer's disease and related conditions.

The methodology of the present invention is useful for diagnosing cerebral amyloidosis and, consequently, the onset and progression of Alzheimer's disease and related conditions and for monitoring the progression of such disease conditions and the effectiveness of therapeutic regimes. In particular, the present invention relates to methods for the detection of protein and non-protein components of DMS and antibodies thereto which, when detected in cerebrospinal fluid, blood or other body fluids, signal the onset or progression of cerebral amyloid plaque formation.

Classified under the rubric "amyloidosis" are a number of pathological conditions characterized by the deposition of abnormal fibrils ("amyloid fibrils") in extracellular spaces. The amyloid fibril, in turn, represents a final common pathway for a diverse array of proteins. Regardless of their biochemical composition, however, all types of amyloid fibrils share (a) a β-pleated sheet structure, (b) green birefringence under polarized light after staining with Congo Red dye, and (c) a fibrillar morphology which has a typical electron-microscopic appearance.

The deposition of amyloid fibrils can affect several organs in the systemic forms of the disorder, exemplified by familial Mediterranean fever, familial amyloid polyneuropathy and systemic amyloidosis, or it can be restricted to one organ in localized forms. Among the latter are conditions classified under the rubric "cerebral amyloidosis," which covers the Alzheimer group of diseases, namely, Alzheimer's disease [pre-senile dementia, senile dementia]; Alzheimer's disease associated with Down's syndrome; Alzheimer's disease associated with other central-nervous-system diseases, such as Parkinson's disorder; and congophilic angiopathy [associated or not associated with Alzheimer's disease].

Alzheimer's disease in general is an incurable brain disease affecting middle aged and elderly people throughout the world. According to most recent estimates, it is the fourth or fifth leading cause of death among North Americans, and is responsible for inestimable personal and social tragedy, loss of productivity, and custodial burden to society. There is presently no widely-accepted effective treatment for Alzheimer's disease.

The principle symptom (manifestation) of Alzheimer's disease is the loss of higher mental faculties, typified by the loss of memory and behavior referred to as "dementia." Dementia is a symptom or syndrome that can be seen in many brain diseases other than Alzheimer's disease, such as stroke, encephalitis and metabolic diseases. Since memory loss and dementia are relatively nonspecific symptoms, a certain and specific definition of Alzheimer's disease is based on the characteristic microscopic state of the brain, described initially by Marinesco, Alzheimer and others. See Alzheimer, A., *Allegemeine Zeitschrift fur Psychiatrie* 64:146–148 (1907); Marinesco, G., *Comptes Rendus des Seances de la Societe de Biologie et ses Filiales* 70:606–608 (1911).

The particular microscopic feature that is a universally accepted indicator of Alzheimer's disease, and that separates Alzheimer's disease from other causes of dementia, is the accumulation of large numbers of brain lesions referred to as senile or amyloid plaques and neurofibrillary tangles. Senile or amyloid plaques are spherical, ranging from 10 to 200 $\mu$m in diameter, and while found only occasionally in aged adult cerebral cortex, are found in large numbers m Alzheimer-affected cortex. These lesions, when found in suitable quantity in a brain sample, are the definitive criteria for the diagnosis of Alzheimer's disease.

The clinical diagnosis of Alzheimer's disease often is a difficult and imperfect task that generally relies initially on ruling out other treatable or clinically definable causes of dementia. In the appropriate clinical context, if the latter causes cannot be proven, Alzheimer's disease is often diagnosed antemortem, by exclusion, as the most probable diagnosis. Many indirect methods of diagnosis at present are being proposed and tested. See Conference Report, Khachaturian, Z., *Arch. Neurol.* 42:1097–1105 (1985). But the only certain and acceptable method for diagnosing Alzheimer's disease is by tissue microscopic histological study of a brain biopsy or necropsy sample, in which the above-mentioned sine qua non lesions are recognized by a certified specialist.

Amyloid plaques in large quantities are essentially found only in the Alzheimer group of diseases, whereas neurofibrillary tangles are nonspecific and are found in at least ten other neurological diseases. See Corsellis, J.A.N., GREENFIELD'S NEUROPATHOLOGY 951–1025 (4th ed. 1984) (Edward Arnold, London). Individual amyloid plaques have roughly 1000× the volume of individual neurofibrillary tangles. True measurements of total brain amyloid plaque and neurofibrillary content are not available, but on the above basis it is likely that the volume of abnormal brain tissue occupied by amyloid plaques is many hundreds of times that of neurofibrillary tangles. The essential feature of the amyloid plaque is the presence of amyloid fibrils, which are a congophilic red-green birefringent microfibrillar material. Corsellis, loc. cit.

A microscopic structure referred to as the dense microsphere (DMS) is known to exist in normal brain and in brain affected by Alzheimer's disease. See Averback, *Acta Neuropathol.* 61:148–52 (1983); results confirmed by Hara, *J. Neuropath. Exp. Neurol.* 45(2):169–178 (1986). Some specialists believe that DMS are linked to cerebral amyloid plaques as the source or as a precursor to the cerebral amyloid characteristic of Alzheimer's disease and related conditions. Evidence for the existence of DMS comes from microscopic histological section studies of fixed whole brain tissue, where the dense microspheres are seen to have a proteinaceous internal or central region ("DMS protein") surrounded by continuous membrane ("DMS membrane"). The dense microspheres are observed as randomly dispersed, highly infrequent structures occupying an estimated $10^{-9}$ or less of total brain volume, at a unit frequency roughly estimated at $10^{-16}$ or less, relative to other definable brain structures such as mitochondria.

The extraction, purification and characterization of isolated samples of DMS nor the use of DMS material to any advantage has only recently been documented. Thus, DMS and its respective components are structures of unproven function and unknown significance or usefulness, and have been effectively unavailable in tangible form.

It is known that DMS, when disrupted in vitro will generate a plurality of components that can be identified using polyacrylamide gel electrophoresis. It is believed that the presence of these components in the cerebrospinal fluid and other body fluids indicates the disruption of DMS in the brain, and consequently, the onset of amyloid plaque formation. Some of the DMS components, however, may be responsible for the formation of amyloid plaques and hence, may not be present in cerebrospinal fluid. Detection of the specific DMS components which are present in cerebrospinal fluid has not been documented.

Moreover, non-surgical procedures for the antemortem diagnosis of cerebral amyloid plaque formation and, consequently, Alzheimer's disease and related conditions have heretofore been limited to the exclusionary process of diagnosis. Confirmation of such disease conditions has been possible only through analysis of brain tissue obtained by biopsy or at autopsy. Immunological methods universally accepted as diagnostic of Alzheimer's disease and related conditions have not heretofore been documented.

SUMMARY OF THE INVENTION

It is therefore an object of the present invention to provide a method for the detection of components of DMS and antibodies thereto in biological samples for the purpose of diagnosing cerebral plaque formation, Alzheimer's disease and related conditions.

It also is an object of the present invention to provide a method of monitoring the progression of cerebral plaque formation, Alzheimer's disease and related conditions by a quantitative analysis of the DMS component content of biological samples.

Another object of the present invention is to provide a method of determining the therapeutic efficacy of a treatment regime for Alzheimer's disease and related conditions by quantitatively analyzing biological samples to determine the content of DMS components and antibodies thereto.

Another object of the present invention is to provide a composition of matter that includes a compound and a pharmaceutically acceptable carrier that is capable of decreasing the amount and/or concentration of DMS components in the cerebrospinal fluid. It is an additional object of the present invention to provide a method of treating Alzheimer's disease, preventing the formation of amyloid plaque and/or preventing the disruption of DMS in a mammal's brain by administering to a mammal suffering from or susceptible to Alzheimer's disease, a composition of matter that includes a compound and a pharmaceutically acceptable carrier that is capable of decreasing the amount and/or concentration of DMS components in the cerebrospinal fluid.

It is yet another object of the present invention to provide components of DMS, as well as antibodies against such components, which can be used in detecting the onset and progression of cerebral plaque formation, Alzheimer's disease and related conditions, even when the individual may not yet have developed clinical symptoms associated with Alzheimer's disease and related conditions.

In accomplishing the foregoing objects, a composition of matter has been provided, in accordance with one aspect of the present invention, wherein the composition consists essentially of DMS components that are detectable in cerebrospinal fluid. In accordance with a further aspect of the present invention, the dense microsphere components are membrane components.

According to another aspect of the present invention, a component of dense microspheres is provided that is the product of a process comprising the steps of:
(a) disrupting or digesting a suspension comprising DMS;
(b) separating the components of the disrupted or digested suspension by polyacrylamide gel electrophoresis; and
(c) isolating the components from the band located at the 5, 8, 10, 12, 16, 19, 21, 25, 28, 30, 31, 33, 40, 45, 48, 52, 60, 66, 70, 80, 100, 110 and 120 kilodalton region of the gel.

According to yet another aspect of the present invention, a component of dense microspheres is provided that is the product of a process comprising the steps of:
(a) obtaining a biological sample of cerebrospinal fluid;
(b) separating the components present in the cerebrospinal fluid by polyacrylamide gel electrophoresis; and
(c) isolating the components from the band located at the 25–27; 28–30; 45–47; 50–53; 55–57; 60–65 and 76–80 kilodalton region of the gel.

In accordance with yet another aspect of the present invention, a composition consisting essentially of an antibody which specifically binds an isolated component of DMS is provided.

According to a further aspect of the present invention, a composition is provided that consists essentially of an antibody which specifically binds an isolated component of DMS, where the component is a product of a process comprising the steps of:
(a) disrupting or digesting a suspension comprising DMS;
(b) separating the components of the disrupted or digested suspension by polyacrylamide gel electrophoresis; and
(c) isolating the components from the band located at the 5, 8, 10, 12, 16, 19, 21, 25, 28, 30, 31, 33, 40, 45, 48, 52, 60, 66, 70, 80, 100, 110 and 120 kilodalton region of the gel is provided.

According to a further aspect of the present invention, a composition is provided that consists essentially of an antibody which specifically binds an isolated component of DMS, where the component is a product of a process comprising the steps of:
(a) obtaining a biological sample of cerebrospinal fluid;
(b) separating the components present in the cerebrospinal fluid by polyacrylamide gel electrophoresis; and
(c) isolating the components from the band located at the 25–27; 28–30; 45–47; 50–53; 55–57; 60–65 and 76–80 kilodalton region of the gel.

In accordance with yet another aspect of the present invention, a composition consisting essentially of an antibody which specifically binds an isolated component of DMS is provided.

In accordance with yet another aspect of the present invention, there is provided a composition consisting essentially of an antibody that specifically binds an isolated component of dense microspheres, the composition further comprising a label selected from the group consisting of a radionuclide, a colorimetric agent and a fluorescent marker.

In accordance with yet another aspect of the present invention, a method for diagnosing cerebral plaque formation, Alzheimer's disease and related conditions is provided, comprising the steps of (a) bringing a biological sample into contact with a first antibody directed against at least one component of dense microspheres; and (b) determining whether the first antibody reacts immunologically with the biological sample.

Pursuant to still another aspect of the present invention, a method for diagnosing cerebral plaque formation, Alzheimer's disease and related conditions is provided, wherein step (a) comprises bringing a biological sample into contact with a first antibody directed against at least one component of dense microspheres; and step (b) comprises the steps of (i) reacting the first antibody with the sample to form antibody/component complexes; (ii) washing the sample to remove any unbound first antibody; (iii) contacting the sample with a labelled second antibody which binds specifically to the first antibody; (iv) washing the sample to remove any unbound labelled second antibody; and then (v) detecting the presence of bound labelled second antibody.

In accordance with a further aspect of the present invention, a method for diagnosing cerebral plaque formation, Alzheimer's disease and related conditions is provided, comprising the steps of (a) bringing a biological sample into contact with at least one component of dense microspheres; and then (b) determining whether the component reacts immunologically with the biological sample.

According to yet a further aspect of the present invention, a method for diagnosing cerebral plaque formation, Alzheimer's disease and related conditions is provided, comprising the steps of (a) bringing a biological sample into contact with at least one component of dense microspheres; and then (b) comprises the steps of (i) washing the sample to remove any unbound components; (ii) contacting a first antibody which is present in the sample, the first antibody being bound to the component, with a labelled second antibody which binds specifically to the first antibody; (iii) washing the sample to remove any unbound second antibody; and then (iv) detecting the presence of bound second antibody.

In accordance with yet a further aspect of the present invention, a method for diagnosing cerebral plaque formation, Alzheimer's disease and related conditions is provided, comprising the steps of (a) bringing a biological sample into contact with at least one component of dense microspheres; and then (b) comprises the steps of (i) washing the sample to remove any unbound components; (ii) contacting a first antibody which is present in the sample, the first antibody being bound to the component, with a labelled second antibody which binds specifically to the first antibody; (iii) washing the sample to remove any unbound second antibody; (iv) detecting the presence of bound second antibody; and then (v) determining the class of the first antibody.

In accordance with another aspect of the present invention, a method for diagnosing cerebral plaque formation, Alzheimer's disease and related conditions is provided, comprising the steps of (a) bringing a biological sample into contact with at least one component of dense microspheres; and then (b) comprises the steps of (i) washing the sample to remove any unbound components; (ii) contacting a first antibody which is present in the sample, the first antibody being bound to the component, with a labelled second antibody which binds specifically to the first antibody; (iii) washing the sample to remove any unbound second antibody; (iv) detecting the presence of bound second antibody; (c) repeating step (b) periodically over time; and (d) determining the quantity and class of antibody directed against the component.

In accordance with yet another embodiment of the present invention, there is provided a method for diagnosing cerebral plaque formation, Alzheimer's disease and related conditions, comprising the steps of (a) bringing a biological sample into contact with a first antibody directed against at least one component of dense microspheres;

(b) determining whether said first antibody reacts immunologically with said biological sample;

(c) determining the quantity of component of dense microspheres present in said biological sample; and (d) repeating steps (a), (b) and (c) periodically and measuring any change in the quantity of component of dense microspheres.

In accordance with a further embodiment of the present invention, there is provided a method for diagnosing cerebral plaque formation, Alzheimer's disease and related conditions, comprising the steps of (a) bringing a biological sample into contact with at least one component of dense microspheres;

(b) determining whether said component reacts immunologically with said biological sample indicating the presence of anti-DMS components in said biological sample;

(c) determining the quantity of anti-DMS components present in said biological sample; and (d) repeating steps (a), (b) and (c) periodically and measuring any change in the quantity of anti-DMS component.

In accordance with another object of the invention there is provided a method of determining the efficacy of an Alzheimer's disease treatment regime comprising the steps of (a) obtaining a sample of cerebrospinal fluid from a patient that is subjected to an Alzheimer's disease treatment regime and (b) measuring the type and quantity of DMS components present in the fluid.

In accordance with a further object of the present invention, there is provided a composition of matter comprising a compound that is effective in preventing the formation of amyloid plaques as measured by a decrease in the quantity and type of DMS components present in cerebrospinal fluid of a patient that to whom the composition of matter had been administered.

In accordance with yet another object of the present invention, there is provided a method of treating Alzheimer's disease, a method of preventing the formation of amyloid plaques and a method of preventing the disruption of DMS in a mammal's brain comprising the step of administering to a mammal a composition of matter comprising a compound that is effective in preventing the formation of amyloid plaques as measured by a decrease in the quantity and type of DMS components present in cerebrospinal fluid of the mammal.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description. Unless otherwise specified, the respective contents of documents cited in the following description are hereby incorporated by reference.

DETAILED DESCRIPTION OF THE PREFERRED EMBODIMENTS

Figure 1:
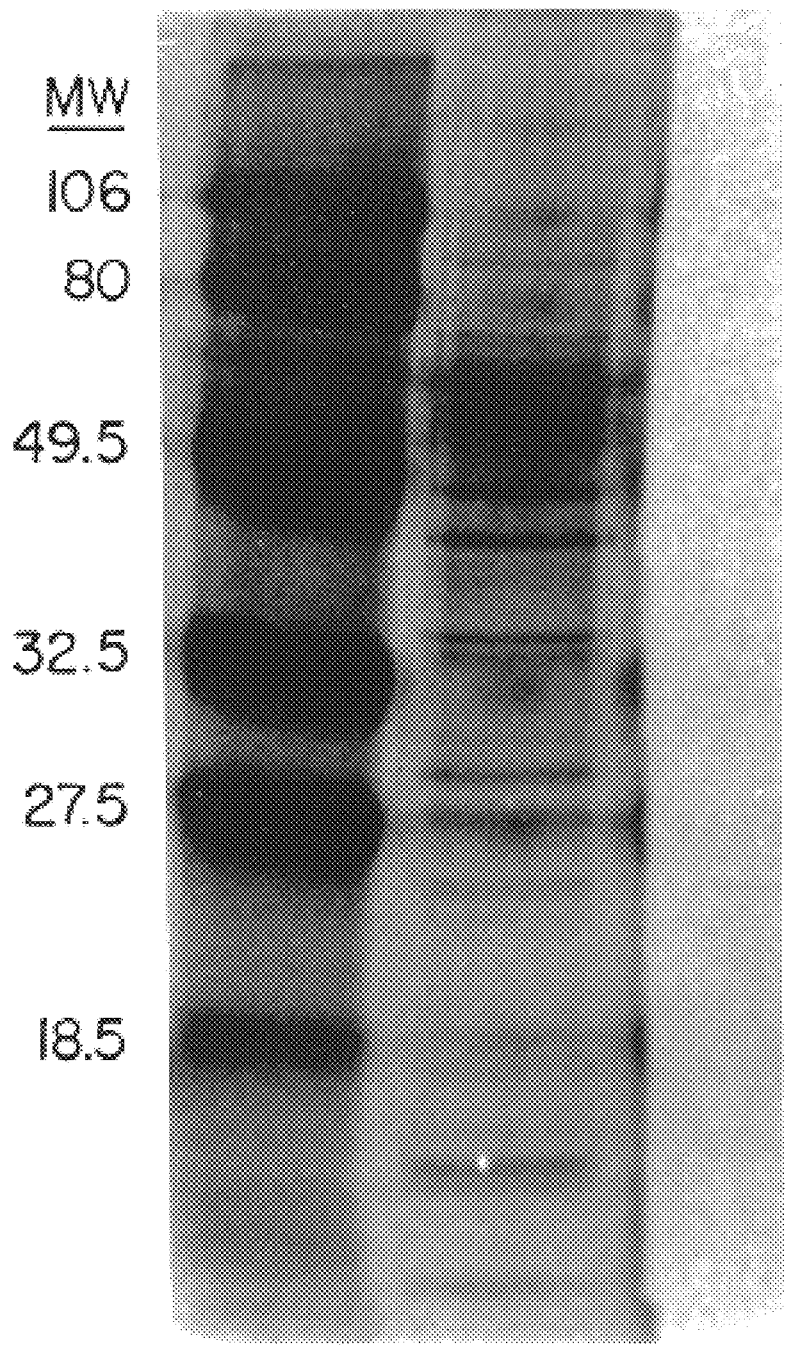
FIG. 1 illustrates a polyacrylamide gel including DMS components obtained by disrupting DMS in vitro and separating the components by molecular weight.

It has been discovered that the disintegration of DMS in the brain parenchyma is associated with the onset and progression of cerebral amyloid plaque formation which is characteristic of Alzheimer's disease and related conditions. More specifically, disintegration of DMS releases protein and non-protein components, or mixtures of protein and non-protein components. A portion of the DMS components form cerebral amyloid plaques, while other portions are removed from the brain parenchyma via circulating bodily fluids, including cerebrospinal fluid, serum and the like.

The presence of DMS components in circulating bodily fluids thus is correlated positively with DMS disintegration and the associated onset of cerebral amyloid plaque formation. Moreover, since DMS are found in the brain, the presence of DMS antigens in circulating bodily fluids and tissue other than brain tissue is correlated positively with DMS disintegration and the associated onset of cerebral amyloid plaque formation. In addition, since DMS are found in the brain, the presence of DMS antigens in circulating bodily fluids will generate autoantibodies in these circulating bodily fluids and tissue other than brain tissue, the generation of which is correlated positively with DMS disintegration and the associated onset of cerebral amyloid plaque formation.

Accordingly, the detection of DMS components and DMS component antibodies in bodily fluids indicates active cerebral amyloid formation. Isolated DMS components pursuant to the present invention can be used as immunogens to produce antibodies which can be employed in conventional immunoassays to detect DMS components in biological samples. Alternatively, DMS components can be utilized in such immunoassays to detect the presence of antibodies directed against DMS components in, for example, serum and other biological fluids. Thus, immunoassays based on DMS components and antibodies thereto can be used in the diagnosis of plaque formation, particularly, cerebral amyloid plaque formation, Alzheimer's disease and related conditions. Such immunoassays can also be employed in monitoring such disease conditions and determining the efficacy of therapeutic regimes by measuring the type and quantity of DMS component and/or DMS component antibody present in circulating bodily fluids.

Throughout this description, the phrase "Alzheimer's disease and related conditions" denotes conditions classified under the rubric "cerebral amyloidosis." Such conditions include, but are not limited to Alzheimer's disease [pre-senile dementia, senile dementia]; Alzheimer's disease associated with Down's syndrome; Alzheimer's disease associated with other central-nervous-system diseases, such as Parkinson's disorder; and congophilic angiopathy [associated or not associated with Alzheimer's disease]. Throughout this description, the phrase "DMS components" denotes any component of DMS, protein, non-protein, or mixtures of protein and non-protein, originating from the internal or central region or from the outer membrane portion of DMS. Throughout this description, the phrase "disrupting" or "digesting a suspension comprising DMS" denotes any process whereby DMS are broken down into DMS components.

DMS present in mammalian brain tissue have an increased tendency to disintegrate into DMS components in individuals susceptible to cerebral amyloidosis. Some of these DMS components are believed to be responsible for forming cerebral amyloid plaques. In addition, when DMS are isolated from mammalian brain tissue in vitro, they have the same tendency to disintegrate. Hence, the disruption of DMS that naturally occurs in individuals susceptible to cerebral amyloidosis can be replicated by isolation of DMS and dissolution in vitro. Furthermore, when a solution containing DMS is injected into an animal for the purpose of raising antibodies against the DMS, the DMS will break down, or disintegrate into DMS components. The antibodies present in the resulting animal serum therefore will be reactive against DMS components.

DMS components can be identified by obtaining a sample of isolated DMS, disrupting the DMS in vitro to simulate the disruption of the DMS in the brain, and then measuring the type and quantity of the DMS components. These components include, for example, components separated on a gel by polyacrylamide gel electrophoresis and isolated, where the band corresponds to a DMS component. The band that is isolated on the gel can be located at a kilodalton region of the gel selected from 5, 8, 10, 12, 16, 19, 21, 25, 28, 30, 31, 33, 40, 45, 48, 52, 60, 66, 70, 80, 100, 110 and 120.

That DMS disintegration is the cause of cerebral plaque formation is supported by the observation that cerebral amyloid plaques appear not only when DMS disappear, but also where DMS disappear; that is, in about the same position in the brain as the now-disrupted DMS. Although the present invention is not restricted by any theory, the protein components of DMS, located in the central or internal region thereof, are believed to be the primary source of the cerebral amyloid plaques. In addition, the DMS membrane components are believed to comprise protein and non-protein matter, as noted above. Accordingly, the presence of DMS membrane components, protein, non-protein or mixtures thereof in bodily fluid will indicate the onset of cerebral plaque formation.

Because some of the DMS components may be responsible for the formation of amyloid plaques and hence, the onset of Alzheimer's disease, it is possible that not all of the DMS components identified by disrupting the DMS in vitro will be present in an identifiable quantity in cerebrospinal fluid and other circulating bodily fluids. The present inventors have found that DMS components present in circulating bodily fluids can be detected by either bringing a solution containing the DMS components in contact with a laboratory made anti-DMS component antibody, or by bringing a bodily fluid containing anti-DMS component antibodies into contact with a solution including laboratory derived DMS components. By carrying out polyacrylamide gel electrophoresis as described herein, the DMS components actually present in identifiable quantities in circulating bodily fluids can be identified using either method. Using the former method, the DMS components can be separated and a band that corresponds to a DMS component can be isolated, whereby the band is located at a kilodalton region of the gel selected from 25–27, 28–30, 45–47, 50–53, 55–57, 60–65 and 76–80 kilodaltons. Using the latter method, the DMS components can be separated and a band that corresponds to a DMS component can be isolated, whereby the band is located at a kilodalton region of the gel selected from 55–60, 62–70 and 82–90 kilodaltons.

In addition to the present inventors belief that circulating bodily fluids may not include all of the DMS components, circulating bodily fluids also already may contain a certain quantity of DMS components without any onset of cerebral plaque formation. In this case, the method of the present invention measures the quantity of DMS components in the bodily fluid periodically. Any dramatic change in the amount of DMS components present therein will indicate the onset of cerebral plaque formation.

Circulating bodily fluids also serve as a convenient source of measuring the efficacy of therapeutic regimes that purport to reduce and/or prevent the formation of amyloid plaques. If a treatment regime, i.e., administration of a therapeutic agent to a mammal in need thereof, prevents the formation of amyloid plaque, then the concentration and type of DMS components present in the bodily fluids will be altered. Hence, the efficacy of the treatment regime can be evaluated simply by measuring the effectiveness of the treatment in reducing the type and concentration of DMS components in the bodily fluids.

The present invention therefore also encompasses a method of treating Alzheimer's disease, a method of preventing the formation of amyloid plaque and a method of preventing the disruption of DMS in a mammal's brain by administering to a mammal a therapeutically effective amount and for a therapeutically effective period of time, a composition of matter that includes a compound effective in treating Alzheimer's disease, preventing the formation of amyloid plaque and/or preventing the disruption of DMS in the brain. The therapeutically effective amount of the compound and the therapeutically effective period of treatment can be readily ascertained by an ordinarily skilled practitioner in this art. The effectiveness of this compound can be ascertained by quantifying the type and concentration of DMS components present in the cerebrospinal fluid of the mammal.

DMS are derived form mammalian brain tissue and are characterized, in essentially homogeneous form, by a range of diameters from about 0.1 $\mu$m to about 15 $\mu$m, by the above-mentioned outer membrane/proteinaceous core structure of DMS, and by certain stainability properties. In this regard, "homogeneous" means that the DMS represent the only structure discernible in the subject composition at the light-microscopic level. For example, the microspheric bodies of the present invention are homogeneously electron-dense when stained with osmium and lead, and can be visualized by thin-section electron microscopy; under optical microscopic examination, they appear eosinophilic and phloxinophilic, and are nonbirefringent when stained with Congo Red. When the microspheric bodies of the present invention are disrupted or disintegrated or digested, a material is produced that displays congophilic birefringence; that is, when stained with Congo Red the material becomes optically anisotropic to the extent of splitting an incident light wave into two waves with mutually perpendicular vibrational planes.

DMS are spherical, membrane-bounded, intracellular structures, about 0.1 $\mu$m to 15 $\mu$m in diameter, that are found in human and other mammalian brains. More specifically, the normal location for DMS is in gray-matter neuropil, where the spherical structures are enclosed in tiny, neuronal cellular processes. DMS are solitary, non-perikayal and non-confluent, and are not found in cerebellum or in white matter. With regard to inter-DMS distances, the spatial distribution of DMS in gray matter regions is random. Compositions of DMS in homogeneous form can be produced by extraction to give homogeneous samples of globular bodies according to procedures described in U.S. Pat. Nos. 4,816,416 and 5,231,170, the entire contents of which are incorporated by reference herein.

The homogeneous composition of dense microspheres prepared according to the above-described procedure can be disrupted by procedures described in the aforementioned U.S. Pat. Nos. 4,816,416 and 5,231,170, and then subjected to differential gradient centrifugation as described therein to separate DMS membrane components from DMS internal components, if desired. Materials isolated in distinct sedimentation layers are stained with Congo Red. The nonbirefringent membrane components can be distinguished from birefringent internal components by microscopic examination. Hence, the present inventor believes that the birefringent internal components are primarily responsible for the formation of cerebral amyloid plaques. Alternatively, DMS membrane components can be distinguished from DMS internal components by electron microscopic examination. The protein and lipid components of DMS membranes can be isolated by conventional extraction methods. Further analysis of lipid DMS membrane components can be accomplished by extraction of such components with organic solvents and by conventional methods such as chromatography that are well-known to those of ordinary skill in the art.

DMS can be treated by a variety of methods to yield DMS components (protein internal components, protein membrane components, non-protein membrane components, or protein and non-protein membrane components) suitable for use according to the present invention. Exemplary of these methods are: (a) PAGE buffer solutions including TRIS, glycerol, $\beta$-mercaptoethanol, bromophenol blue and sodium dodecyl sulfate (SDS), (b) ultrasonication and (c) other proteolytic treatments such as treating with various combinations of 0.25M acetic acid, 6M guanidine HCl, formic acid, 6M urea, pepsin and cyanogen bromide. The resulting homogeneous composition of DMS components can be further refined by isolating the components according to their molecular weight by polyacrylamide gel electrophoresis (PAGE) or according to the degree of their hydrophobicity by reverse phase high performance liquid chromatography (rpHPLC). DMS components isolated by PAGE can be further characterized as either discrete migrating or non-migrating components. DMS components also can be extracted from cerebrospinal fluid and other bodily fluids using the extraction procedures described above.

In accordance with the present invention, DMS components isolated by PAGE or rpHPLC can be employed in conventional immunoassays to detect the presence of antibodies to DMS components in serum, cerebrospinal fluid and other fluids or tissues. Immunoassays within the present invention include but are not limited to, ELISA-type assays [see, for example, VOLLER et al., THE ENZYME LINKED IMMOSORBENT ASSAY (ELISA) (Dynatch Laboratories, Inc. 1979)], Western Blot, and other immunological tests, such as radioimmunoassays and conventional immunoprecipitin assays, for detecting DMS components in biological samples. See Ausbel et al., CURRENT PROTOCOLS IN MOLECULAR BIOLOGY (John Wiley & Sons, New York 1990), the contents of which are incorporated by reference.

Via conventional techniques, as described, for example, by Kennet et al., Curr. Top. Microbiol. Immunol. 81:77–91 (1978), anti-DMS component antibodies can be produced using the isolated DMS components of the present invention and then "labelled" with a radionuclide, a colorimetric agent or a fluorescent marker. The labelled antibodies can be used in diagnostic tests to screen for the presence of DMS components in serum, cerebrospinal fluid and other fluids and tissues. The presence of such components in these bodily fluids is indicative of cerebral DMS disintegration and the associated onset of cerebral amyloid plaque formation. A decrease in type and quantity of DMS components in these bodily fluids likewise in indicative of the effectiveness of a therapeutic regimen. In this context, the term "antibody" encompasses monoclonal and polyclonal antibodies. Such an antibody can belong to any antibody class (IgG, IgM, IgA, etc.). For monoclonal antibody (Mab) production, one generally proceeds by isolating lymphocytes and fusing them with myeloma cells, producing hybridomas. The cloned hybridomas are then screened for production of "anti-DMS component" antibodies, that is, antibodies that bind preferentially to a DMS component. "Antibody" also encompasses fragments, like Fab and $F(ab')_2$, of anti-DMS antibodies, and conjugates of such fragments, and so-called "antigen binding proteins" (single-chain antibodies) which are based on anti-DMS antibodies, in accordance, for example, with U.S. Pat. No. 4,704,692, the disclosure of which is hereby incorporated by reference in its entirety.

Alternatively, Mabs or fragments thereof within the present invention can be produced using isolated DNA which codes for variable regions of such an Mab in host cells like *E. coli,* see Ward et al., Nature 341:544–546 (1989), or transfected murine myeloma cells, see Gillies et al., *Biotechnol.* 7:799–804 (1989), and Nakatani et al., loc. cit., 805–810. In addition, Fab molecules can be expressed and assembled in a genetically transformed host like *E. coli.* A lambda vector system is available thus to express a population of Fabs with a potential diversity equal to or exceeding that of the subject generating the predecessor antibody. See Huse et al., *Science* 246:1275–1281 (1989).

Antibodies against DMS components can also be employed in the generation, via conventional methodology, of ant-idiotypic antibodies (antibodies that bind an anti-DMS antibody), for instance, by the use of hybridomas as described above. See, for example, U.S. Pat. No. 4,699,880.

The above-described materials, including DMS components and antibodies thereto that react specifically to indicate the presence of DMS components or anti-DMS antibodies, can thus be employed in immunoassays which can be used to detect DMS disruption, or disintegration in the brain, and which can be used to detect the efficacy of a treatment regimen. Such testing could be used, in accordance with the present invention, in the context of providing a method for the detection of such materials for the purpose of diagnosing and monitoring cerebral plaque formation, particularly, cerebral amyloid plaque formation, Alzheimer's disease and related conditions. More specifically, the progress of such disease conditions could be monitored by determining, via conventional methods, the specific class and quantity of any antibody present in a biological sample over an extended period of time. See, for example, Nisonoff, A., INTRODUCTION TO MOLECULAR IMMUNOLOGY 14–15 (Sinauer Associates 1982).

Alternatively, such testing could be used in the context of providing a method for determining the therapeutic efficacy of a treatment regime for Alzheimer's disease and related conditions by quantitatively analyzing biological samples for the presence of DMS components or antibodies thereto. Diagnostic testing of this sort can be conducted by assaying, immunologically or otherwise, for the presence of DMS components such as DMS membrane (protein, nonprotein or both), DMS protein or fragments thereof in biological samples not derived from brain tissue, e.g., samples of serum, cerebrospinal fluid and other bodily fluids or tissues. Testing can also be directed to detection in a subject of antibodies against one or more DMS components. In addition, prophylactic therapy according to the present invention can be administered to the nondemented population on the basis of other factors, suggesting a risk for dementia, which are revealed by radiological or diagnostic imaging, genetic testing, electroencephalography or other means.

Additionally, diagnostic testing can be used in the context of providing a method for measuring the quantity of DMS components in biological fluids periodically. Any dramatic increase in the quantity of DMS components indicates the onset of cerebral plaque formation and, consequently, the risk of Alzheimer's disease and related conditions.

Other details of the present invention are further described by reference to the following illustrative examples.

EXAMPLE 1

In Vitro Isolation of Components of DMS by Polyacrylamide Gel Electrophoresis

DMS were isolated from human brains by density gradient centrifugation according to the methodology described in U.S. Pat. Nos. 4,816,416 and 5,231,170. The concentrated sediment containing isolated DMS then was subjected to digestion or disruption and separation by the following methods.

About 100 µg of solution containing purified DMS was suspended in 50 µl of a PAGE buffer consisting of 0.5M TRIS (pH 6.8), glycerol, β-mercaptoethanol, 0.4% bromophenol blue solution and sodium dodecyl sulfate (SDS). The solubilized preparation was electrophoresed on a 15% acrylamide gel with a resolving buffer consisting of TRIS (pH 6.8) and an electrode buffer consisting of TRIS base (pH 8.6), glycine and SDS at 150V for 4 hours. See Laemmli, U.K., *Nature* 227:680 (1970). The gel was stained with silver using a BioRad® Kit according to the manufacturer's instructions. Bands containing the DMS components of interest are presented in FIG. 1.

In FIG. 1, lane A is the molecular weight standard and lane B is a preparation of DMS components described above. The bands containing the protein fragments of primary interest are located in the 5, 8, 10, 12, 16, 19, 21, 25, 28, 30, 31, 33, 40, 45, 48, 52, 60, 66, 70, 80, 100, 110 and 120 kilodalton region.

In addition to the bands containing isolated protein components, the homogenous composition of DMS components subjected to PAGE is also comprised of certain nonmigrating components.

The individual DMS component fractions listed above can be separated by conventional mechanisms well known to those skilled in the art. For example, a microfiltration, ultrafiltration or reverse osmosis apparatus can be used with various molecular weight cut-off membranes to separate the individual DMS components. Additionally, gels produced in accordance with Example 1 can be cut between the distinct bands thereby separating the DMS components. The individual DMS components then can be recovered from the gel by conventional means such as solvent precipitation and the like.

Depending on the particular antigen present on the aforementioned DMS components, these components can be stained by anti-DMS by well known methods including Western Blot. Alternatively, these DMS components can be isolated as described above and used as pure immunogens for antibodies, which in turn are used to identify specific protein fragments by staining and other methods described above.

EXAMPLE 2

Preparation of Antibodies to DMS and Evaluation of the Presence of DMS Antigens in Cerebrospinal Fluid A DMS antibody was prepared by inoculation of a rabbit with pure DMS prepared in accordance with Example 1, mixed at a molar ratio of 1:1 with Freund's complete adjuvant. Two hundred $\mu$l of mixture was injected subcutaneously, with 100 $\mu$l booster injections at 8 week intervals. The DMS injected into the rabbits disintegrated into DMS components in solution either in the rabbit or prior to injection. The rabbits were bled at intervals and serum was separated. The resulting solution containing the rabbit anti-DMS then was tested to determine the presence of anti-DMS by ELISA with pure DMS components or pure DMS, and by Western Blot techniques.

Cerebrospinal fluid (50 $\mu$l) was extracted from a patient with Alzheimer's disease and blotted onto a nitrocellulose filter. The filter was then was blotted with 5% albumin solution and incubated for 24 hours with rabbit anti-DMS at 1:100 molar dilution, in 5% albumin solution. The filter then was incubated with 1:1000 diluted horseradish peroxidase goat anti-rabbit IgG in 5% albumin for 1 hour at room temperature. The filter was washed with phosphate buffered saline and stained. The filter was positively stained indicating the presence of DMS antigens in the patient's cerebrospinal fluid.

The presence of DMS antigens in the patient's cerebrospinal fluid indicates the presence of DMS components that contain one or more DMS antigens. The amount of DMS antigen present in the patient's cerebrospinal fluid then can be calculated using known techniques such as serial dilution followed by ELISA and the like.

Analogously to Example 1, cerebrospinal fluid extracted from a patient with Alzheimer's disease was applied to a 10% polyacrylamide gel in denaturing buffer and the material was separated into its component proteins. The gel separated cerebrospinal proteins then were transferred to nitrocellulose paper. A Western blot then was developed from the paper with anti-DMS and stained as described above with horseradish peroxidase and substrate. The banding pattern on the polyacrylamide gel exhibited reactivity in the following molecular weight regions: 25–27; 28–30; 45–47; 50–53; 55–57; 60–65 and 76–80 kildoDaltons.

The presence of some, but not all DMS components described in Example 1 above in the cerebrospinal fluid indicates that these selective bands are a subgroup of DMS components that have a more selective and hence unexpected, diagnostic utility than the other DMS components, and that antibodies to these components include a subgroup of anti-DMS antibodies that have a more selective diagnostic utility than other anti-DMS antibodies. This example illustrates the identification of a group of DMS components by measuring the DMS components in a body fluid using a laboratory-derived anti-DMS.

EXAMPLE 3

Evaluation of the Presence of Anti-DMS in Serum and Spinal Fluid

By means of a nitrocellulose blot method similar to Example 2, cerebrospinal fluid and serum from six patients with Alzheimer's disease were incubated on nitrocellulose filters previously blotted with pure DMS. Positive staining in each case indicated the presence of anti-DMS in serum and spinal fluid. The presence of anti-DMS in the serum and spinal fluid indicates the presence of DMS components therein. Thus, the presence of anti-DMS in serum and spinal fluid indicates cerebral amyloid plaque formation and, consequently, the onset or existence of Alzheimer's disease.

By means of a Western blot procedure similar to that described above in Example 2, DMS components were separated in 10% polyacrylamide gel and transferred to nitrocellulose paper, and then reacted with a mixture of cerebrospinal fluid diluted 10-fold in Tris buffered with saline with 5% Carnation dry milk. The blot was reacted with anti-human IgG conjugated with peroxidase and substrate. The banding pattern showed immunoreactivity at the regions of approximately 55–60; 62–70 and 82–90 kiloDaltons.

The presence of selective anti-DMS activity in cerebrospinal fluid as above to only some DMS components indicates that these selective DMS components are a subgroup of DMS components that have a more selective diagnostic utility than the other DMS components described in Example 1 above. This example illustrates the identification of a group of DMS components using laboratory mixtures of DMS components and body fluid derived auto-anti-DMS.

EXAMPLE 4

Preparation of Antibodies to DMS Components and Evaluation of the Presence of DMS Component Antigens in Cerebrospinal Fluid DMS components are prepared in accordance with the methods outlined in Example 1 above and purified. The purified DMS components then are subjected to the procedures of Examples 2 and 3 to raise antibodies specific to the DMS components and to evaluate the presence of anti-DMS components in the cerebrospinal fluid and serum of patients with Alzheimer's disease. The formation of plaque, particularly cerebral amyloid plaque formation, Alzheimer's disease and related conditions can be diagnosed in accordance with this method.

EXAMPLE 5

Preparation of a Composition that is Effective in Preventing Amyloid Plaque Formation as Indicated by a Decrease in the Type and Quantity of DMS Component Antigens or Anti-DMS Antibodies in Cerebrospinal Fluid The present inventors believe that the presence of an increased concentration of DMS components in cerebrospinal fluid correlates with the onset of cerebral plaque formation and hence, the onset of Alzheimer's disease. A composition that is effective in preventing the formation of cerebral plaque therefore would result in a decrease in the concentration of DMS components or antibodies thereto in the cerebrospinal fluid. This example evaluates the efficacy of a treatment regime for treating Alzheimer's disease in a mammal.

Subjects suspected to have DMS disintegration in the brain and resultant DMS component formation or intracerebral amyloid, or to be at risk of having intracerebral amyloid are tested for the presence and quantity of DMS components and anti-DMS auto-antibodies in their cerebrospinal fluid, blood or other bodily fluid. The baseline DMS component and anti-DMS auto-antibody levels or concentrations are measured by periodically extracting samples of cerebrospinal fluid from the mammals and measuring the type and quantity of DMS components and anti-DMS antibodies in accordance with the procedures outlined in Examples 2–4 above. This procedure is repeated a few times monthly to evaluate the baseline concentration for the particular DMS components present in the mammals bodily fluids.

A test compound is administered (orally, parenterally, intranasally or by other means) to the mammal in a therapeutically efficacious amount and for a therapeutically effective period of time. At various time intervals on a monthly basis after commencing administration of the test compound, the type and concentration of DMS components and anti-DMS auto-antibodies are measured in accordance with the procedures outlined above. The type and concentrations of DMS components and antibodies thereto then are compared to the baseline levels determined above. A decrease in the concentration of DMS components or anti-DMS auto-antibodies or the complete disappearance thereof correlates with the effectiveness of the compound in entering the brain, binding to DMS or fragments thereof in the brain and preventing and/or inhibiting the disintegration of DMS. Hence, test compounds that are shown to be effective in decreasing the type and concentration of DMS components and/or antibodies thereto is useful in inhibiting cerebral amyloid formation from disintegration of DMS.

The invention has been described with reference to the foregoing examples which exemplify preferred embodiments. Those skilled in the art recognize that various modifications can be made to the present invention without departing from the spirit and scope thereof.

What is claimed is:

1. A method of detecting the quantity of antibodies to DMS components present in a biological sample, comprising:
   (a) contacting a biological sample with at least one component of dense microspheres (DMS) having a molecular weight selected from the group consisting of 8, 10, 12, 16, 19, 21, 25, 28, 30, 31, 33, 40, 45, 48, 52, 60, 66, 70, 80, 100, 110, and 120 kilodaltons; and
   (b) determining the immunoreactivity of said component with said biological sample,
   wherein the quantity of antibodies to DMS components in the biological sample corresponds to the immunoreactivity of the DMS component with the biological sample.

2. A method according to claim 1, wherein step (b) comprises the steps of
   (i) washing said sample to remove any components that have not displayed immunoreactivity to the at least one component of dense microspheres;
   (ii) contacting a first antibody which is present in said sample, said first antibody being bound to said component, with a labeled second antibody which binds specifically to said first antibody;
   (iii) washing said sample to remove any unbound second antibody; and then
   (iv) detecting the presence of bound second antibody.

3. The method as claimed in claim 1, wherein the antibody specifically recognizes an isolated component of DMS having a molecular weight selected from the group consisting of 8, 10, 12, 16, 19, and 21 kilodaltons.

4. The method as claimed in claim 1, wherein the antibody specifically recognizes an isolated component of DMS having a molecular weight selected from the group consisting of 30, 31, 33, 40, 45, 48, 52, 60, 70, 100, 110, and 120 kilodaltons.

5. A method of detecting the quantity of DMS components in a biological sample comprising:
   (a) contacting a biological sample with a first antibody that specifically recognizes at least one component of dense microspheres (DMS) having a molecular weight selected from the group consisting of 8, 10, 12, 16, 19, 21, 25, 28, 30, 31, 33, 40, 45, 48, 52, 60, 66, 70, 80, 100, 110, and 120 kilodaltons; and
   (b) determining the immunoreactivity of said first antibody with said biological sample,
   wherein the quantity of DMS components in the biological sample corresponds to the immunoreactivity of the first antibody with the biological sample and wherein the antibody specifically recognizes an isolated component of DMS having a molecular weight of 8 kildodaltons.

6. A method of detecting the quantity of DMS components in a biological sample comprising:
   (a) contacting a biological sample with a first antibody that specifically recognizes at least one component of dense microspheres (DMS) having a molecular weight selected from the group consisting of 8, 10, 12, 16, 19, 21, 25, 28, 30, 31, 33, 40, 45, 48, 52, 60, 66, 70, 80, 100, 110, and 120 kilodaltons; and
   (b) determining the immunoreactivity of said first antibody with said biological sample,
   wherein the quantity of DMS components in the biological sample corresponds to the immunoreactivity of the first antibody with the biological sample and wherein the antibody specifically recognizes and isolated component of DMS having a molecular weight of 10 kildodaltons.

7. A method of detecting the quantity of DMS components in a biological sample comprising:
   (a) contacting a biological sample with a first antibody that specifically recognizes at least one component of dense microspheres (DMS) having a molecular weight selected from the group consisting of 8, 10, 12, 16, 19, 21, 25, 28, 30, 31, 33, 40, 45, 48, 52, 60, 66, 70, 80, 100, 110, and 120 kilodaltons, and
   (b) determining the immunoreactivity of said first antibody with said biological sample,
   wherein the quantity of DMS components in the biological sample corresponds to the immunoreactivity of the first antibody with the biological sample and, wherein the antibody specifically recognizes an isolated component of DMS having a molecular weight selected from the group consisting of 8, 10, 12, 16, 19, and 21 kilodaltons.

* * * * *